United States Patent [19]

Krill et al.

[11] Patent Number: 6,005,147
[45] Date of Patent: Dec. 21, 1999

[54] METHOD OF PRODUCING 3, 5, 5-TRIMETHYLCYCLOHEXA-3-ENE-1-ONE(β-ISOPHORONE) BY THE ISOMERIZATION OF 3, 5, 5-TRIMETHYLCYCLOHEXA-2-ENE-1-(α-ISOPHORONE)

[75] Inventors: Steffen Krill, Speyer, Germany; Günes Giray, Mavischir-Didim, Turkey; Klaus Huthmacher, Geinhausen, Germany; Frank Hübner, Ober-Ramstadt, Germany; Herbert Tanner, Hanau, Germany

[73] Assignee: Degussa Aktiengesellschaft, Frankfurt, Germany

[21] Appl. No.: 08/938,822

[22] Filed: Sep. 26, 1997

[30] Foreign Application Priority Data

Sep. 26, 1996 [DE] Germany .............................. 19639570

[51] Int. Cl.⁶ .................................................. C07C 45/67
[52] U.S. Cl. ........................................... 568/341; 568/347
[58] Field of Search ...................... 568/341, 347

[56] References Cited

U.S. PATENT DOCUMENTS 4,845,303  7/1989  Bellut ..................................... 568/441
4,970,191  11/1990  Schutz ..................................... 568/345
5,276,197  1/1994  Nosberger et al. ..................... 568/341
5,545,761  8/1996  Dawson et al. ........................ 568/342

FOREIGN PATENT DOCUMENTS 0 488 045    6/1992   European Pat. Off. .
2 074 410   12/1970   France .
01 175954    7/1989   Japan .

*Primary Examiner*—James H. Reamer
*Attorney, Agent, or Firm*—Pillsbury Madison & Sutro LLP

[57] ABSTRACT

A method of producing 3,5,5-trimethylcyclohexa-3-ene-1-one (β-isophorone) including a catalyst of an oxide or mixed oxide of at least one element of the groups IIa, VIII, Ib, IIIa and Va of the periodic system. Isomerization is carried out without the addition of an organic base. The space-time yield in the production of β-isophorone by the isomerization of α-isophorone is at a level suitable for an industrial application. β-isophorone is especially suitable as an intermediate product for producing ketoisophorone.

21 Claims, No Drawings

METHOD OF PRODUCING 3, 5, 5-TRIMETHYLCYCLOHEXA-3-ENE-1-ONE(β-ISOPHORONE) BY THE ISOMERIZATION OF 3, 5, 5-TRIMETHYLCYCLOHEXA-2-ENE-1-(α-ISOPHORONE)

CROSS-REFERENCE TO RELATED APPLICATION

This application claims priority from German Patent Application No. 19639570.4, filed Sep. 26, 1996, the subject matter of which is hereby incorporated herein by reference.

FIELD OF THE INVENTION

The invention relates to a method of producing 3,5,5-trimethylcyclohexa-3-ene-1-one (β-isophorone) by the isomerization of 3,5,5-trimethylcyclohexa-2-ene-1-one (α-isophorone) in the liquid phase in the presence of a heterogeneous catalyst.

BACKGROUND OF THE INVENTION

β-isophorone has great economic significance since it is an important synthetic structural element for the production of carotinoids, vitamins and pharmaceutical products. In particular, β-isophorone is required as a precursor for ketoisophorone(2,6,6-trimethylcyclohex-2-ene-1,4-dione) and trimethylhydroquinone and therewith for the production of vitamin E. In addition, it is pivotably used in syntheses for odorous substances and natural compounds such as astaxanthine and abscisic acid and derivatives.

The production of isophorone is carried out by means of acetone trimerization under condensation of the C₃ structural elements. The primarily formed isomer is α-isophorone since it has, in contrast to the β isomer, a double bond conjugated to the keto function. For this reason the thermodynamic equilibrium is on the side of the α-isophorone; the β concentration is only approximately 1–2% and the adjustment of equilibrium takes place very slowly.

Although there are basically two different preparations for arriving at ketoisophorone, namely, the direct oxidation of α-isophorone (α-IP)→ketoisophorone (KIP) and the indirect route via the isomerization α-isophorone→β-isophorone (β-IP) in a primary step and subsequent oxidation of the β-isophorone→ketoisophorone, the latter process is clearly advantageous. Scheme 1 presents these considerations for ketoisophorone synthesis in a clear manner.

Scheme 1 : General reaction scheme for the synthesis of KIP (ketoisophorone = 2,6,6-trimethyl-2-cyclohexene -1,4-dione

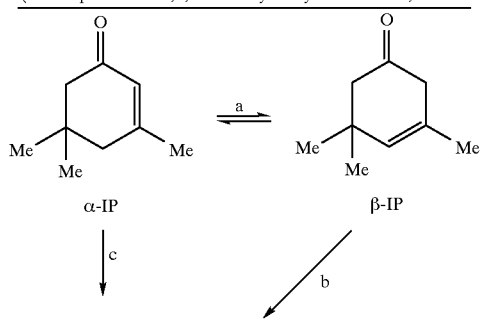

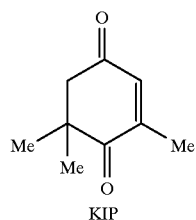

KIP a = Isomerization of α-IP to β-IP
b = Oxidation of β-IP to KIP
c = Direct oxidation α-IP to KIP Numerous methods for the isomerization of α-IP have been described in the course of time which, however, have significant disadvantages. Viewpoints such as consumption of chemicals, poor space/time yields and problems in the workup have prevented, up to the present, a practical processing reaction on a rather large scale.

A distinction between gaseous phase reactions and liquid phase reactions can be drawn in the production methods for β-IP from α-IP.

Basically, four parallel reactions of α-isophorone are possible in the gaseous phase which compete with one another and can be used to a varying degree as a function of the selected temperature range and of the nature of the surface of the catalyst used.

Isophorone can react in the following manner on contact in the gaseous phase:

a.) Isomerization to β-isophorone
b.) Reduction to trimethylcyclohexadienes (hydrogen required for this is supplied by isophorone (IP) decomposition accompanied by carbonization phenomena)
c.) β-Elimination of methane to 3,5-xylenol
d.) Production of mesitylene.

The following scheme 2 shows the reactions of α-IP catalyzed upon heterogeneous contact in the gaseous phase:

Scheme 2 : Reactivity of α-IP in the heterogeneous gaseous-phase catalysis

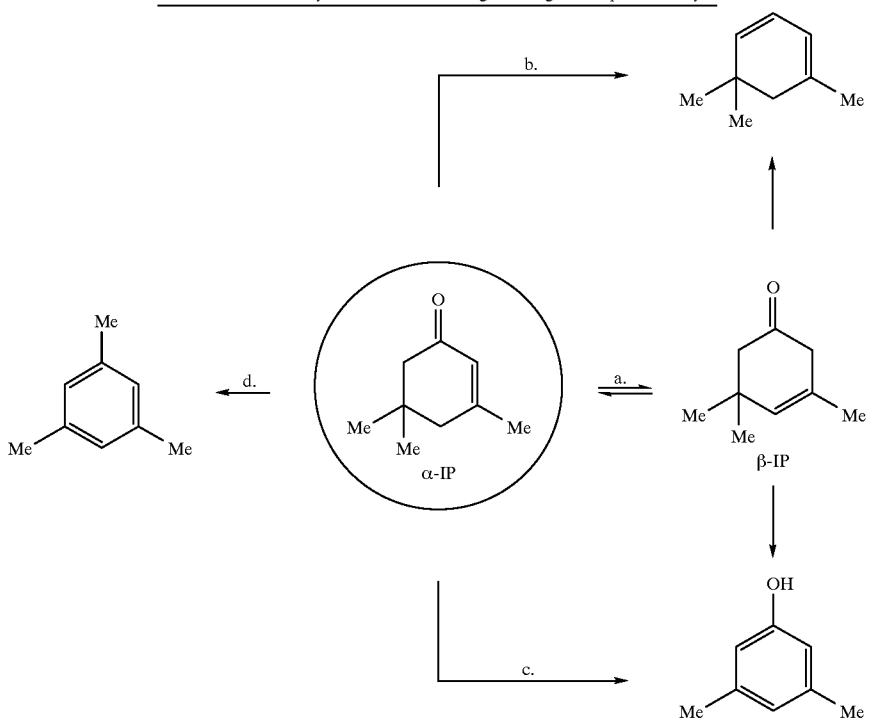

EP 0,488,045 B1 discloses an isomerization method in the gaseous phase (300–450° C.) with a heterogeneous catalyst. Oxides and mixed oxides of Mg (group IIa), Al (IIIa), Si (IVa) and Ni (VIII) are used as catalysts which are active per se or are applied on a γ-aluminum oxide carrier (specific surface 1–50 m²/g). 1–10 kg α-IP are used per liter catalyst, the concentration of the intermediately obtained solution is about 9% β-IP, the final concentration after distillation in a vacuum is 97% β-IP. The granulation of NiO takes place with 1% Luviskol K90 (-polyvinylpyrrolidone). This result corresponds, relative to the amount of catalyst used and the time, to a yield of Y=0.308 kg β-IP per liter catalyst and hour. A disadvantage to this is the fact that only a 9% β-IP mixture accumulates per hour. The space-time (S-T) yield $Y_{S-T}=0.09$ $1_{\beta\text{-}IP}/1_{solution}$ relative to the educt volume used (example 1).

In addition, the rate of removal is low, which makes the method not very attractive on an industrial scale.

L. F. Korzhova, Y. V. Churkin and K. M Vaisberg, Petrol. Chem. Vol. 31, 1991, 678 describe the reaction of α-IP at 300–800° C. in the presence of heterogeneous catalysts. γ-Aluminum oxide, magnesium oxide and quartz are considered as catalytic systems. The product spectrum is observed as a function of temperature and of catalyst. The formation of β-IP, trimethylcyclohexadiene, 3,5-xylenol and of mesitylene are compared with each other (see scheme 2: Paths a., b., c., d.). Thus, the thermal reaction of α-IP at above 550° C. on a slightly developed catalytic surface (quartz) results in a mixture of the composition c>>a>>d and b=0. The reaction of the MgO contact at 400° C. shows a similar product distribution at distinctly lower temperature, namely, c>>a>d>b. The reaction takes place at 300° C. in the presence of an aluminum oxide catalyst with pronounced basic-acidic surface structure with a distinct preference given to the cyclohexadiene products, namely, b>>c>d.

On the whole, it can be assumed that a catalytic gaseous-phase isomerization is absolutely disadvantageous in several ways: It can be stated in general that these methods are disadvantageous because either the product formation is accompanied by a considerable accumulation of byproducts or the space-time yield (absolute β-IP production/$hkg_{cat}$) is too low.

A number of publications also relate to the isomerization in the liquid phase. The recent state of the art is represented by the following publications:

D1=A. Heymes et al., Recherches 1971, 18, 104
D2=FR-A-1,446,246
D3=DE-OS-24 57 157
D4=U.S. Pat. No. 4,005,145
D5=EP-A-0,312,735
D6=JP 87-33019 corresp. to HEI-1-175954 of Jul. 12, 1989.

D1 discloses the isomerization of α-IP to β-IP with stoichiometric amounts of MeMgX (Me=methyl; X=halogen) Grignard compound. 73% β-IP is obtained under the evolution of methane in the presence of catalytic amounts of $FeCl_3$. Mechanistic notions start with the assumption that the Grignard compound reacts as a base and does not function as the carrier of a carbanion. Excess Mg results in the production of dimer mixtures which proceed from a reductive metallic dimerization. However, the reaction of α-isophorone with molar amounts of methylmagnesium iodide in the presence of catalytic amounts of $FeCl_3$, subsequent hydrolysis and workup by distillation is just as complicated as it is in the consumption of chemicals.

D2 relates to the isomerization of α-IP to β-IP in the presence of catalytic amounts of p-toluene sulfonic acid and generally aromatic sulfonic acids, especially aniline sulfonic acid. The amount of the catalyst used is 0.1–0.2% relative to the (α-IP used. However, a low degree of conversion and a high accumulation of byproducts prevent an industrial application of the method of D2.

According to D3, the preparation of β-IP takes place by means of boiling α-IP for several hours in triethanol amine, fractionation, washing the distillate with tartaric acid and sodium chloride solution. The consumption of chemicals is also considerable here.

In D4, acids with a pK=2–5 and a higher boiling point than β-IP (boiling point β-IP=186° C./760 mm Hg) are used as catalyst. According to the patent claim the following are explicitly protected in the liquid phase:

Aliphatic and aromatic amino acids, adipic acid, p-methylbenzoic acid, 4-nitro-m-methylbenzoic acid, 4-hydroxybenzoic acid, 3,4,5-trimethoxybenzoic acid, vanillic acid, 4-trifluoromethylbenzoic acid, 3-hydroxy-4-nitrobenzoic acid and cyclohexane carboxylic acid and derivatives. The amount of catalyst used is 0.1–20 molar percent. The yield of β-IP (relative to α-IP used) is 74.5%. This corresponds under the given conditions converted to the amount of catalyst used and time to a yield of Y=0.218 liters β-IP per kilogram catalyst and hour.

The homogeneous catalytic isomerization of α-IP→β-IP with slightly dissociated acids represents an improvement as concerns the consumption of chemicals with β-IP being continuously removed from the equilibrium. With so low a rate of removal as 11 ml/h β-IP from an educt volume of approximately 0.5 kg α-IP, the space-time yield and the production of β-IP with Y=0.24 kg β-IP/kg$_{cat}$ are too low to be used in technological applications.

A similar principle is followed in D5. Acetyl acetonates of transitional metals are used as π bond isomerization catalysts. Even Al (acac) displays catalytic activity. The use of the catalyst takes place in 0.01–10% by weight. Metallic catalysts of the groups IVb (Ti/Zr/Hf), Vb (V/Nb/Ta), VIb (Cr, Mo, W), VIIb (Mn/Tc/Re), of the entire group VIII and aluminum are patented. The primarily accumulating distillate has a β-IP content of 94%, a further Vigreux distillation enriches the β-IP content to 99%. This result corresponds, relative to amount of catalyst used and the time, to a yield of Y—9.4 liters β-IP per kilogram catalyst and hour. This corresponds, relative to the educt solution used, to a yield of $Y_{s-t}=0.0376 \, 1_{\beta\text{-}IP}/h/1_{solution}$.

Aside from the fact that the space-time yield is low and the accumulation of byproducts considerable, catalyst and distillation residue can not be readily separated in the homogeneous catalytic system used. Therefore, discarding is from time to time necessary since the temperature in the distillation bottom would otherwise rise too high. Even so, a "re-truing" of the temperature is required.

According to D6, the isomerization takes place in the liquid phase at temperatures around 200° C. Silica gels with or without the addition of alkyl-substituted imidazolines of the following formula are used as catalyst.

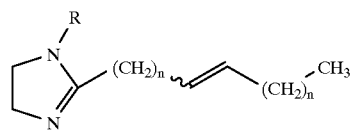

Typical experimental conditions: 300 g α-IP and 25.7 g SiO$_2$ are distilled for 52 h in the presence of refined steel; 230 g β-IP (=76.6% yield) result with 99.0% purity. This result corresponds, relative to amount of catalyst used and the time, to a yield of Y=0.174 liters β-IP per liter catalyst and hour.

However, the preparation of the organic bases is expensive and the space-time yield of the method low; with a characteristic value of Y=0.174 liters β-IP/l catalyst per hour, even this method can not be converted to a technical scale. Relative to the volume of educt solution used the yield is $Y_{s-t}=0.0149 \, 1_{\beta\text{-}IP}/h/1_{solution}$.

Moreover, the procedure described is unfavorable and the absolute production of β-IP is low. The batchwise reaction and the performance of the isomerization reaction and pure distillation of the β-IP in one step is especially disadvantageous. It can be demonstrated that the re-isomerization of β-IP to α-IP occurs to a considerable extent on account of the high reaction temperature in the distillation apparatus.

SUMMARY OF THE INVENTION

In view of the state of the art cited and discussed herein, the invention has, as the problem to be solved, the avoidance of the above-mentioned disadvantages of the previous methods and the offering of a method according to which 3,5,5-trimethylcyclohexa-3-ene-1-one can be produced from its isomer 3,5,5-trimethylcyclohexa-2-ene-1-one in a technically advantageous manner. A particular goal of the invention is to find a heterogeneous catalytic method in the liquid phase.

These and other problems not individually indicated are solved by the method described.

DETAILED DESCRIPTION OF THE INVENTION

As a result of the fact that an oxide or mixed oxide of an element of the groups IIa, VIII, Ib, IIIa and Va of the periodic table is used and that the isomerization is carried out without the addition of an organic base it is possible in a way which could not have been readily foreseen to raise the space-time yield in the production of β-isophorone by the isomerization of α-isophorone to a level suitable for industrial use and at the same time to distinctly simplify a process known from the state of the art.

The method of the invention makes possible a high conversion in the range of approximately 9 kg α-isophorone per kg catalyst used and per hour and exceeds therewith the methods previously known in the state of the art. Furthermore, according to the invention both the accumulation of byproducts is reduced and the space-time yield improved, relative to the volume of educt solution used. Viewed in its totality, the use of the heterogeneous catalyst of the invention is advantageous in every instance.

A method is used in the present invention in which α-isophorone is reacted to its isomer β-isophorone using a heterogeneous catalyst in the liquid phase.

A procedure is especially advantageous in which the reaction and the product isolation do not take place in the same apparatus. The space-time yield can be clearly increased by first producing a mixture of α-IP and β-IP in an isomerization unit and then carrying out the pure distillation in a vacuum since at a concentration of β-IP at normal pressure and a boiling temperature of 186° C. partial re-isomerization occurs which is prevented by rapidly removing the reaction mixture from the reaction area.

Oxides or mixed oxides of an element of the groups IIa, VIII, Ib, IIIa and Va of the periodic system of elements or also salts of said elements such as, in particular, carbonates or halides, which salts are insoluble under test conditions, are used as heterogeneous catalysts in the sense of the invention. The group division of the main and secondary groups of the periodic system of elements takes place according to the designation in accordance with IUPAC, Pure and Appl. Chem., 66, 2423–2444, 1994. Thus, the metals Be, Mg, Ca, Sr, Ba and Ra are in group IIa; the metals Fe, Co, Ni, Ru, Rh, Pd, Os, Ir and Pt are in group VIII; and the elements Cu, Ag, Au, B, Al, Ga, In, Tl, N, P, As, Sb and Bi are in groups Ib, IIIa and Va.

The compounds which can be used in accordance with the invention as heterogeneous catalysts include the oxides or mixed oxides of the above-named elements. The term mixed oxides signifies a compound in this connection in which oxygen forms a compound with more than one of the cited elements.

The oxides which can be used within the scope of the invention include BeO, MgO, CaO, SrO, BaO, $TiO_2$, $ZrO_2$, $MoO_3$, $Fe_3O_4$, $Fe_2O_3$, CoO, $CO_3O_4$, NiO, $PdO_2$, $PtO_2$, ZnO, $Al_2O_3$, $SiO_2$.

The mixed oxides which can be used within the scope of the invention also include, in addition to mixed compounds of the oxides cited above, among others $Al_2O_3/SiO_2$ and zeolites of various modules, e.g. H-ZSM-5.

Of the oxides or mixed oxides indicated above those preferred in particular contain an element of groups IIa or VIII of the periodic system.

Oxides or mixed oxides of calcium and/or magnesium are specially preferred within the scope of the invention.

In a further embodiment of the method of the invention it is preferred that an oxide or mixed oxide of cobalt and/or nickel is used.

Quite especially preferred oxides are, among others, $CO_3O_4$ as well as MgO and CaO.

Another catalyst which is especially preferred is $\gamma$-$Al_2O_3$.

Cobalt carbonates and nickel carbonates, optionally in their hydrate form, are especially suitable.

In addition to the use of oxides or mixed oxides as heterogeneous catalysts in accordance with the invention for the isomerization of $\alpha$-isophorone to $\beta$-isophorone, even oxides and mixed oxides of the groups IIa, VIII, Ib, IIIa and Va of the periodic system of elements doped with elementary metals can be used with good success. Elements, especially metals, from the same groups of the periodic system can be used for the doping. The doping metals preferably used include, among others, the metals of groups VIII and Ib. In a special variation, the method of the invention is characterized in that a catalyst is used which is doped with a metal from group VIII of the periodic system. Within group VIII the metals cobalt and/or nickel are especially favorable as doping metals.

The amount of metal used for doping is not especially critical and can therefore be varied over a broad range. It is preferred that the doping metal is used in an amount of 0.1 to 50% by weight (wt/wt) relative to the oxide or mixed oxide. An especially favorable catalyst is obtained if a $\gamma$-$Al_2O_3$ or $Co_3O_4$ doped with nickel and/or cobalt is used.

Furthermore, the catalyst or also the catalyst doped with a metal can be present in pure form or fixed on a carrier material or mixed with the carrier, which carrier material can be one of the described catalysts. Other carrier materials are known to one skilled in the art. They include carriers such as $\alpha$-$Al_2O_3$, $\gamma$-$Al_2O_3$, $SiO_2/Al_2O_3$ of different modules, aluminum salts such as e.g. aluminum silicates and aluminum phosphates, activated carbon, etc.

Even the amount of the catalyst to be used for the isomerization can basically be varied over a rather large range. It is preferred that the catalyst is used in a ratio between 0.01 and 30% by weight (wt/wt) relative to $\alpha$-isophorone. In an especially preferred variant of an embodiment the method of the invention is characterized in that the catalyst is used in a ratio of between 0.2 and 10% by weight (wt/wt) relative to $\alpha$-isophorone.

In yet another especially preferred embodiment the ratio of catalyst to $\alpha$-isophorone is in a range between 0.5 and 5% by weight (wt/wt).

The method of the invention is carried out over a temperature range between 100 and 300° C. The temperature range between 150 and 260° C. is preferred.

The addition of a thinning agent or solvent is possible but not required.

The reaction is preferably carried out at a pressure of 10 mbar to 3 bar excess pressure. Quite especially favorable isomerization parameters are about 100 mbar to normal pressure (approximately 1 hPa) at the boiling temperature of $\alpha$-isophorone.

The method of the invention can be advantageously operated in a continuous manner. In a preferred embodiment, the isomerization and the pure distillation are separated from one another. The liquid phase containing the isomerizate is distilled under a vacuum after it has been separated off in order to separate $\alpha$-isophorone and $\beta$-isophorone.

The distillation then takes place at temperatures at which the temperature sensitive re-isomerization is largely excluded.

It is advantageous to recycle the bottom product of the distillation into the isomerization stage.

The supply of $\alpha$-isophorone is 2.3–70 l $\alpha$-IP/h/kg cat with a 5–60% mixture of $\beta$-IP/$\alpha$-IP being taken off at the top of the isomerization unit. This mixture is subsequently subjected to vacuum distillation with a $\beta$-IP product with a purity >97% accumulating. The bottom product of the column is returned without purification to the isomerization unit. It is possible in this way to produce, converted, 9.182 kg $\beta$-IP/kg cat/h. This result exceeds that of the previously described methods. The novel method is also clearly superior to the state of the art as regards the accumulation of byproducts (in comparison e.g. to reference D1, where stoichiometric amounts of Grignard compound are consumed) and the space-time yield relative to the volume of the educt solution. In addition, the use of a heterogeneous catalyst brings significant advantages in separating off the high boiling fraction from the catalytic material. Known methods (e.g. EP 312,735) display distinct disadvantages here which do not appear in the method of the invention. A filtration and post-treatment or regeneration of the catalyst with a small amount of solvent (e.g. $\alpha$-IP itself) is completely sufficient.

EXAMPLE 1

Commercial $Co_3O_4$ (obtained from the Merck company) (Co(II/III)oxide) is used. The form of catalyst used is powdery in this instance but a granulated form is also catalytically active. Pretreatment of the catalyst is not necessary. The apparatus for carrying out the isomerization consists of a closed-circuit heater heated with two electrically supplied rod inserts. 700 ml industrial $\alpha$-isophorone is placed in a receiver (Atochem company >98%) and 25 g $Co_3O_4$ added. A distillation column 1.2 m long with an inside diameter of 25 mm filled with V4A Raschig rings of 4 mm Ø rests above the closed-circuit heater. The suspension is heated at normal pressure up to boiling temperature. The amount of $\alpha$-IP, supplied via a Telab pump, and the amount of the distillate taken off are coordinated with one another. The following $\beta$-IP content is adjusted in the primary distillate as a function of the rate of distillate taken off, as shown below:

| Rate of taking off distillate | 20 ml/h | 40 ml/h | 80 ml/h | 120 ml/h | 160 ml/h | 260 ml/h |
|---|---|---|---|---|---|---|
| β-IP content (ml) | 47.3 | 44.4 | 38.9 | 33.6 | 26.8 | 19.0 |
| Production of β-IP/h(ml/h) | 9.4 | 17.7 | 31.1 | 40.4 | 43.5 | 49.5 |

The bottom temperature of the isomerization unit remains constant during the reaction period at 216–217° C. The accumulating primary distillate is delivered to a distillation column operating at a vacuum of 5 mbar–100 mbar. The top product accumulating at 12 mbar has a boiling point of 55–58° C. and consists of >97% of β-isophorone. At the described conditions of the example, 50 g β-isophorone are produced per hour. The α-isophorone non-reacted as the bottom product has a residual β-IP content <3% and is returned to the isomerization unit. The selectivity relative to the conversion is >98%. The yield relative to the amount of catalyst used is $Y=1.98\ l_{\beta\text{-}IP}/h/kg_{cat}$. The space-time yield ($Y_{s-t}$) relative to the volume of the solution to be isomerized is $Y_{s-t}=0.0707\ l_{\beta\text{-}IP}/h/l_{solution}$.

EXAMPLE 2

25 g of a magnesium oxide catalyst are filled into the apparatus already described. A primary distillate with the following composition is taken off, using the same continuous method of operation (see Example 1), at the top of the isomerization unit in accordance with the rate of taking off the distillate shown below:

| Rate of taking off distillate | 40 ml/h | 120 ml/h | 240 ml/h |
|---|---|---|---|
| β-IP content (ml) | 46.0 | 34.8 | 21.5 |
| Production of β-IP (ml/h) | 18.4 | 41.8 | 51.6 |

The amount of β-IP produced can be optimized by further raising the rate of removal. The bottom temperature of the isomerization unit remains constant at 216–217° C. for the time of the reaction. The yield relative to the amount of catalyst used is $Y=2.064\ l_{\beta\text{-}IP}/h/kg_{cat}$. The space-time yield relative to the educt solution used is $Y_{s-t}=0.0737\ l_{\beta\text{-}IP}/h/l_{solution}$.

EXAMPLE 3

1.160 l α-IP are reacted on 4.4 g $Co_3O_4$ catalyst (cobalt black $Co_3O_4$; MW=240.8 g/mol; 4.4 g=18.3 mmol) (IP= 138.21 g/mol; 1/160 ml=8.393 mmol) in the described apparatus (same dimensioning of the isomerization as example 1). Primary distillates with the following β-IP content are obtained as a function of the rate of taking off the distillate:

| Rate of taking off distillate | 20 ml/h | 40 ml/h | 80 ml/h | 160 ml/h | 240 ml/h | 280 ml/h |
|---|---|---|---|---|---|---|
| β-IP content (ml) | 52.6 | 47.3 | 40.4 | 25.9 | 16.6 | 14.7 |
| Production of β-IP/h(ml/h) | 10.5 | 18.9 | 32.2 | 41.4 | 39.8 | 41.2 |

The bottom temperature of the isomerization unit remains constant at 216–217° C. The yield relative to the amount of catalyst used is $Y=9.363\ l_{\beta\text{-}IP}/h/kg_{cat}$. The space-time yield relative to the educt solution used is $Y_{s-t}=0.0588\ l_{\beta\text{-}IP}/h/kg_{cat}$.

EXAMPLE 4

Instead of the cobalt oxide catalyst of Example 3, α-aluminum oxide (Hoffmann La Roche Co. A2) is added in the isomerization unit. The reaction is carried out analogously to Example 1. α-IP/β-IP mixtures of the following composition are obtained with continuous removal of distillate:

| Rate of taking off distillate | 20 ml/h | 40 ml/h | 95 ml/h | 160 ml/h | 180 ml/h |
|---|---|---|---|---|---|
| β-IP content (ml) | 58.4 | 34.5 | 17.6 | 12.2 | 9.7 |
| Production of β-IP/h (ml/h) | 11.7 | 13.8 | 16.7 | 19.5 | 17.5 |

The isomerization is carried out at a constant bottom temperature of 216–217° C. The yield relative to the amount of catalyst used is $Y=0.78\ l_{\beta\text{-}IP}/h/kg_{cat}$. The space-time yield relative to the educt solution used in $Y_{s-t}=0.0278\ l_{\beta\text{-}IP}/h/l_{solution}$.

EXAMPLE 5

$Co_3O_4$ (Merck Company) is used, without pretreatment, as the catalyst. The dimensioning of the apparatus corresponds to that of the previous examples, the stoichiometric ratios of catalyst/α-IP correspond to the conditions of Example 1. The pressure and temperature of the isomerization are varied and the β-IP content of the primary distillate accumulating at the top of the column is examined at a constant rate of taking off the distillate of 120 ml/h. The isomerization temperatures associated with the corresponding pressures can be gathered from the table.

| Temperature bottom (° C.) | Pressure (mbar) | β-IP content (vol. %) |
|---|---|---|
| 216 | 1000 | 33.8 |
| 203 | 770 | 25.8 |
| 192 | 580 | 18.6 |
| 178 | 390 | 14.6 |

EXAMPLE 6

The apparatus described in Examples 1–5 is operated semi-continuously (non-reacted α-IP is not brought into contact with the catalyst again) and the isomerization unit is filled with 25 g $Co_3O_4$ (Merck company). Then, a total of 11 l industrial α-IP are continuously charged with a Telab laboratory pump during which an approximately 20% by volume β-IP/α-IP mixture accumulates as primary distillate. The bottom temperature of the isomerization unit remains a constant 216–217° C. during the reaction. The rate of taking off the distillate is around 250 ml/h, which corresponds to a production of β-IP of 50 (ml β-IP/h). 905 g of a thin oil remain as bottom product, 117 g (12.9%) of which consists of overcondensates and 87.1% of which consists of recoverable α-IP. The accumulation of byproduct relative to α-IP reacted is thus 5.3%.

EXAMPLE 7

The apparatus described in Examples 1–5 is operated continuously. The isomerization unit is connected to the distillation column via a Telab pump. The α-IP accumulating in the bottom of the distillation unit is taken off via an overflow container and returned to the isomerization unit. A β-isophorone with a purity >97% is taken off at the top of the distillation column. 3.7 lα-IP (Atochem: >98% GC) is reacted in this manner. 25 g cobalt black (Merck company) is used as catalyst, the rate of taking off the distillate is 240–250 ml/h and the isomerization temperature is 216–217° C. The primary mixture has a β-IP content of 20–22%. During the reaction time the catalyst shows no aging and can be almost completely recovered at the end of the reaction by filtration (23.3 g $Co_3O_4$). After the end of the reaction, 555 g α-IP and 60 g high boilers remain in the forced-circulation reboiler, which can be readily separated by distillation. 3.07 kg β-IP (purity ~98%) is obtained as distillate. The yield relative to the conversion is thus 97.6%. The accumulation of byproduct is 1.9%. The remainder consists of water which is produced by α-IP dimerization or condensation or which passes through by means of the industrial educt into the reaction.

EXAMPLE 8

50 g CaO are added as catalyst into a 2-l three-neck flask with KPG agitator and 120 cm Vigreux column set on top and 1.5 lα-isophorone placed in the flask. The pressure of the apparatus is lowered to 350 mbar, during which the liquid begins to boil at an inside temperature of 175–180° C. The three-neck flask is additionally equipped with a dropping funnel which permits continuous adding of α-IP. The addition of fresh α-IP corresponds to the amount of α-IP/β-IP mixture taken off at the top of the Vigreux column. 200 ml isomeric mixture is continuously taken off, the β content of which is approximately 21–22% by weight. The mixture being produced is distilled in a vacuum, the α-IP accumulating in the bottom of the pure distillation is returned to the catalyst. β-IP product with a purity >98% can be taken off at the top of the pure distillation. 3 kg α-IP are reacted with the procedure, yielding 2,850 g of a >98% β-IP product. The selectivity, relative to reacted α-IP, is >95%. The catalyst is still active after regeneration by filtration and washing with α-IP and can be used for another cycle. The yield relative to the amount of catalyst used is $Y=0.88\ l_{\beta\text{-}IP}/h/kg_{cat}$. The space-time yield relative to the educt solution used is $Y_{s-t}=0.0293\ l_{\beta\text{-}IP}/h/kg_{solution}$.

EXAMPLE 9

The apparatus described in Examples 1 to 6 is operated discontinuously. 25 g silica gel 60 (Merck 7734) is used as catalyst, the isomerization reboiler is filled with 300 g (325 ml) α-isophorone. An α-IP/β-IP mixture with the following composition accumulates at the top of the isomerization unit as a function of the rate of taking off the distillate:

| Rate of taking off distillate | 80 ml/h | 120 ml/h | 220 ml/h |
|---|---|---|---|
| β-IP content (ml) | 37.5 | 22.8 | 13.1 |
| Production of β-IP (ml/h) | 30 | 27.36 | 28.8 |

The reaction is carried out at normal pressure and temperatures of 216–217° C. bottom temperature. In the test arrangement presented above the yield relative to amount of catalyst used is $Y=1.2\ l_{\beta\text{-}IP}/h/kg_{cat}$. The space-time yield relative to the educt solution used is $Y_{s-t}=0.0923\ l_{\beta\text{-}IP}/h/l_{solution}$.

If the procedure described in Japanese Offenlegungsschrift (A) HEI 1-175954 is followed (300 g α-IP; 25.7 g $SiO_2$, rate of decrease 5 g/h) and an 89% β-IP/α-IP mixture/h is drawn off using $SiO_2$ as catalyst, the yield relative to the amount of catalyst is $Y=0.174\ kg_{\beta\text{-}IP}/h/kg_{cat}$. The space time yield relative to the educt solution used is $Y_{s-t}=0.0149\ l_{\beta\text{-}IP}/h/kg_{solution}$.

EXAMPLE 10

The same apparatus as is described in Example 9 is used and 5% by weight $CoCO_3$ (cobalt carbonate, AMG Kokkola company) used as catalyst. The formation rate of β-IP is 67 g/h/l at a rate of taking off the distillate of 25% by vol. of the α-IP mixture used. A selectivity of S=98% is determined by quantification of the high-boiler portion produced.

What is claimed is:

1. A method of producing 3,5,5-trimethylcyclohexa-3-ene-1-one (β-isophorone) by isomerization of 3,5,5-trimethylcyclohexa-2-ene-1-one (α-isophorone) in a liquid phase in the presence of a heterogeneous catalyst, wherein oxide, mixed oxide, carbonate or halide of at least one element of groups IIa, VIII, Ib, IIIa and Va of the periodic system or salts of these elements, which salts are insoluble under the reaction conditions, is used as catalyst and isomerization is carried out without addition of an organic base.

2. The method according to claim 1, wherein an oxide or mixed oxide of at least one element of the groups IIa and VIII of the periodic system is used as catalyst.

3. The method according to claim 2, wherein an oxide or mixed oxide of Ca and/or Mg is used as catalyst.

4. The method according to claim 2, wherein an oxide or mixed oxide of Co and/or Ni is used as catalyst.

5. The method according to claim 4, wherein $Co_3O_4$ is used as catalyst.

6. The method according to claim 1, wherein the catalyst is doped with at least one metal from group VIII of the periodic system.

7. The method according to claim 6, wherein the catalyst is doped with Ni and/or Co.

8. The method according to claim 6 wherein the at least one doping metal is used in an amount of 0.1–50% by weight (wt/wt) relative to the oxide or mixed oxide.

9. The method according to claim 6, wherein a $\gamma\text{-}Al_2O_3$ or $Co_3O_4$ doped with Ni and/or Co is used as catalyst.

10. The method according to claim 1, wherein a carbonate or halide of said elements is used as catalyst.

11. The method according to claim 10, wherein a cobalt carbonate or nickel carbonate, optionally in hydrate form, is used as catalyst.

12. The method according to claim 1 wherein the catalyst is used in a ratio of between 0.01 and 30% by weight (wt/wt) relative to α-isophorone.

13. The method according to claim 10, wherein the catalyst is used in a ratio of between 0.2 and 10% by weight (wt/wt) relative to α-isophorone.

14. The method according to claim 10, wherein the catalyst is used in a ratio of between 0.5 and 5% by weight (wt/wt) relative to α-isophorone.

15. The method according to claim 1, wherein the isomerization is carried out at temperatures between 100 and <300° C., preferably 150–260° C., during which the pressure is such that the liquid phase is maintained.

16. The method according to claim 15, wherein the isomerization is carried out at normal pressure of approximately 1 hPa and at boiling temperature of α-isophorone.

17. The method according to claim 1, wherein isomerized liquid phase is distilled in order to separate α-isophorone and β-isophorone.

18. The method according to claim 17, wherein a bottom product of the distillation is recycled into the isomerization.

19. The method according to claim 17, wherein the isomerization is continuously operated.

20. The method according to claim 1, wherein the isomerization is carried out at a temperature of 150 to 260° C. and a pressure of 1000 to $1.5 \times 10^5$ Pa, reaction mixture is continuously drawn off and distilled at a pressure of 100 to $3 \times 10^4$ and distillation bottom optionally returned into the isomerization.

21. The method according to claim 20, characterized in that the reaction mixture is drawn off at an amount of 5 to 95% by weight/h.

* * * * *